United States Patent
Lorant et al.

(10) Patent No.: US 9,717,670 B2
(45) Date of Patent: *Aug. 1, 2017

(54) COSMETIC COMPOSITION COMPRISING MATTIFYING FILLERS AND A SILANE

(71) Applicant: L'OREAL, Paris (FR)

(72) Inventors: Raluca Lorant, Thiais (FR); Nathalie Guillier, Vigneux sur Seine (FR); Mathieu Chabrillangeas, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/395,883

(22) PCT Filed: Apr. 24, 2013

(86) PCT No.: PCT/EP2013/058516
§ 371 (c)(1),
(2) Date: Oct. 21, 2014

(87) PCT Pub. No.: WO2013/160362
PCT Pub. Date: Oct. 31, 2013

(65) Prior Publication Data
US 2015/0118270 A1    Apr. 30, 2015

Related U.S. Application Data

(60) Provisional application No. 61/658,090, filed on Jun. 11, 2012, provisional application No. 61/652,652, filed on May 29, 2012.

(30) Foreign Application Priority Data

Apr. 26, 2012 (FR) ..................... 12 53865
Apr. 26, 2012 (FR) ..................... 12 53866

(51) Int. Cl.
*A61K 8/58* (2006.01)
*A61Q 19/00* (2006.01)
*A61K 8/02* (2006.01)
*A61K 8/25* (2006.01)
*A61K 8/26* (2006.01)

(52) U.S. Cl.
CPC ............ *A61K 8/585* (2013.01); *A61K 8/0241* (2013.01); *A61K 8/25* (2013.01); *A61K 8/26* (2013.01); *A61Q 19/00* (2013.01); *A61Q 19/007* (2013.01); *A61Q 19/008* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 5,900,393 A * | 5/1999 | Ramachandran | A61K 8/44 424/70.19 |
| 2006/0093564 A1* | 5/2006 | Russ et al. | 424/63 |
| 2006/0110351 A1* | 5/2006 | Koehler et al. | 424/70.12 |
| 2008/0044370 A1* | 2/2008 | Goino | A61K 8/97 424/74 |
| 2008/0233071 A1* | 9/2008 | Hentrich et al. | 424/70.122 |
| 2008/0311398 A1 | 12/2008 | Bauer et al. | |
| 2009/0247648 A1* | 10/2009 | Zhao | 514/772 |
| 2011/0195100 A1 | 8/2011 | Bruning et al. | |

OTHER PUBLICATIONS

Standeker et al., "Adsorption of toxic organic compounds from water with hydrophobic silica aerogels", Journal of Colloid and Interface Science 310 (2007) 362-368.

Martin et al., "Co-continuous morphology and stress relaxation behaviour of unfilled and silica filled PP/EPDM blends", Materials Chemistry and Physics 113 (2009) 889-898.

Gottschalck et al., The Cosmetic, Toiletry and Fragrance Association: "International Cosmetic Ingredient Dictionary and Handbook", Jan. 1, 2010, vol. 4, pp. 4571, 4704, 4891.

* cited by examiner

Primary Examiner — Jianfeng Song
(74) Attorney, Agent, or Firm — Polsinelli PC

(57) ABSTRACT

The present invention relates to a composition comprising an aqueous phase, at least one mattifying filler and at least one silane corresponding to formula (I) below and/or oligomers thereof: $R_1Si(OR_2)_z(R3)_x(OH)_y$ (I) in which: •Ri is a linear or branched, saturated or unsaturated C1-C22 hydrocarbon-based chain, which may be substituted with an amine group NH2 or NHR (R=C1-C20 and especially C1-C6 alkyl, C3-C40 cycloalkyl or C6-C30 aromatic); or with a hydroxyl group, a thiol group, an aryl group (more particularly benzyl), which is substituted or unsubstituted; Ri possibly being interrupted with a heteroatom (O, S or NH) or a carbonyl group (CO), •R2 and R3, which may be identical or different, represent a linear or branched alkyl group comprising from 1 to 6 carbon atoms, •y denotes an integer ranging from 0 to 3, and •z denotes an integer ranging from 0 to 3, and •x denotes an integer ranging from 0 to 2, •with z+x+y=3, The invention also relates to a cosmetic process for making up and/or caring for keratin materials comprising a step of applying a composition according to one of the preceding claims to the said materials.

8 Claims, No Drawings

COSMETIC COMPOSITION COMPRISING MATTIFYING FILLERS AND A SILANE

CROSS REFERENCE TO RELATED APPLICATIONS

This application is a National Phase filing under 35 U.S.C. §371 of PCT/EP2013/058516 filed on Apr. 24, 2013; and this application claims priority to application Ser. No. 1253865 filed in France on Apr. 26, 2012 and application Ser. No. 1253866 filed in France on Apr. 26, 2012; and this application claims the benefit of U.S. Provisional Application No. 61/652,652 filed on May 29, 2012, and U.S. Provisional Application No. 61/658,090 filed on Jun. 11, 2012. The entire content of each application is hereby incorporated by reference.

The invention relates to a cosmetic composition for keratinous substances, in particular the skin and the lips, the hair and the nails. The invention also relates to a cosmetic process for treating keratin materials using the said composition.

In the field of cosmetic skincare compositions, it is known practice to use soft-focus mineral or organic fillers that absorb sebum and perspiration, in order to make the skin matt and/or to optically smooth out the microrelief and hide skin imperfections.

However, the use of these fillers is generally accompanied by a dry, rough feel and a lack of comfort that is unacceptable for the user.

Silicone elastomers are also widely used as mattifying agents because they make it possible to obtain a soft feel on the skin, but they must be used at a relatively high content in order to have the mattifying effect, which constitutes a curb on the choice of the texture and on the cost of the formulation.

However, there is still a need for cosmetic compositions that have mattifying/absorbent effects on the excess of sebum or moisture and/or that make it possible to mask skin imperfections, and which have good cosmetic properties, in particular which are soft on application and are less restrictive in terms of cost. Moreover, a sensation of comfort during application and a silky skin feel after penetration are also sought.

The Applicant has discovered that this need can be satisfied by combining in a composition at least mattifying fillers and a particular silane.

More specifically, one subject of the present invention is a cosmetic composition comprising:
  an aqueous phase,
  at least one mattifying filler, and
  at least one silane corresponding to formula (I) below and/or oligomers thereof:

$$R_1Si(OR_2)_z(R_3)_x(OH)_y \quad (I)$$

in which:
  $R_1$ is a linear or branched, saturated or unsaturated C1-C22 hydrocarbon-based chain, which may be substituted with an amine group $NH_2$ or NHR (R=C1-C20 and especially C1-C6 alkyl, C3-C40 cycloalkyl or C6-C30 aromatic); or with a hydroxyl group, a thiol group, an aryl group (more particularly benzyl), which is substituted or unsubstituted; $R_1$ possibly being interrupted with a heteroatom (O, S or NH) or a carbonyl group (CO),
  $R_2$ and $R_3$, which may be identical or different, represent a linear or branched alkyl group comprising from 1 to 6 carbon atoms,
  y denotes an integer ranging from 0 to 3, and
  z denotes an integer ranging from 0 to 3, and
  x denotes an integer ranging from 0 to 2,
  with z+x+y=3,
  the silane(s) of formula (I) and/or oligomers thereof are present in an active material content ranging from 2% to 20% by weight relative to the total weight of the composition.

A subject of the invention is also a cosmetic composition that may be obtained by mixing at least one silane as described above and at least one mattifying filler.

The mixture of mattifying fillers and silane makes it possible to obtain compositions that are comfortable and soft on application, which spread easily and which have mattifying and soft-focus properties.

Another subject matter of the invention is the use of the said composition in the cosmetic or dermatological field, and in particular for caring for, protecting and/or making up bodily or facial skin, or for haircare.

In that which follows, the expression "at least one" is equivalent to "one or more" and, unless otherwise indicated, the limits of a range of values are included within this range.

Mattifying Filler:

The term "fillers" should be understood as meaning colourless or white, mineral or synthetic particles of any shape, which are insoluble and dispersed in the medium of the composition irrespective of the temperature at which the composition is manufactured.

These fillers, which are mineral or organic in nature, make it possible to confer, on the composition, softness, mattness and uniformity on the skin.

The fillers used in the compositions according to the present invention may be in lamellar (or platelet), spherical (or globular) form, in the form of fibres or in any other intermediate form between these defined forms.

In the present patent application, the term "spherical particles" means particles in the form or substantially in the form of a sphere, which are insoluble in the medium of the composition according to the invention, even at the melting point of the medium (about 100° C.).

The term "lamellar particles" means herein particles of parallelepipedal shape (rectangular or square surface), discoid shape (circular surface) or ellipsoid shape (oval surface), characterized by three dimensions: a length, a width and a height, these particles being insoluble in the medium of the composition according to the invention, even at the melting point of the medium (about 100° C.).

The mineral and/or organic mattifying fillers are preferably chosen from diffusing fillers.

The term "fillers" means divided solid particles, i.e. particles in powder form. These fillers generally have a volume-median diameter of less than 15 μm.

For the purposes of the invention, the term "diffusing filler" denotes a spherical or non-spherical, porous or non-porous particle with a refractive index of less than or equal to 2, especially less than or equal to 1.8 and preferably ranging from 1.3 to 1.6. The refractive index of the particles may be evaluated by the contrast erasure method. By choosing two totally miscible solvents with relatively remote refractive indices (ethanol: 1.36, and phenylethyl alcohol: 1.529), it is possible to prepare mixtures having intermediate refractive indices. The particles under consideration are suspended in these various solvent mixtures and the transparency of these solutions is then evaluated using a Hach 2100P® turbidimeter sold by the company Hach. The refractive index of the particle is equal to that of the solvent mixture for which the least turbid solution is obtained, i.e.

the solution with the least cloudiness and which corresponds to the minimum refractive index difference between the particles and the solvent mixture.

The "diffusing fillers" according to the invention generally have a volume-median diameter of less than 15 μm.

In one preferential embodiment of the invention, the "diffusing fillers" are spherical.

In one preferential embodiment of the invention, the "diffusing fillers" are porous. In this case, the specific surface area of the particles, which may be related to the porosity, is greater than 10 m2/g and preferably greater than 50 m2/g.

The specific surface area per unit of mass can be determined by the nitrogen absorption method, known as the BET (Brunauer-Emmett-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

In one preferential embodiment of the invention, the "diffusing fillers" are mattifying and/or "soft-focus" fillers.

The term mattifying or "soft-focus" filler means a filler which gives the complexion more transparency and a hazy effect and give the skin a good appearance, without conferring on it a greasy, gleaming and shiny appearance. To do this, fillers generally termed mattifying fillers are used, which are most often absorbent fillers such as talc, silica, kaolin or fillers having light scattering optical properties, which properties are known under the name "soft focus" effect.

In the particular case in which the fillers under consideration according to the invention are mattifying or "soft-focus" fillers, the mattifying power of the compositions containing them may be characterized by means of the following protocol.

The test composition is spread out at a rate of 2 mg/cm$^2$ on a contrast card (Prufkarte type 24/5-250 cm$^2$ sold by the company Erichsen) using a mechanical film spreader. The composition is then dried overnight at a temperature of 37° C. prior to measurement of its reflection using a gonioreflectometer sold by the company Micromodule. The intensity reflected specularly at 30° (R) and scattered at 90° (D) are successively measured. The result obtained is the ratio R between the specular reflection and the diffuse reflection. The value of R is proportionately smaller the greater the mattifying effect afforded by the filler.

In the context of the present invention, a value of R of less than or equal to 2 generally indicates a mattifying effect. The mattifying fillers according to the invention are those which, preferably at a content of 5% in a cosmetic composition, give a value of R of less than 1.5 and preferably less than 1.

More particularly, these mattifying fillers may be chosen, for example, from:
  silicas,
  clays,
  silicate derivatives,
  hydrophobic silica aerogel particles,
  porous silica microparticles, for instance the Silica Beads SB150 and SB700 from Miyoshi with a mean size of 5 microns; the Sunsphere Series-H products from Asahi Glass, for instance Sunsphere H33, H51 and H53 with respective sizes of 3, 5 and 5 μm,
  polytetrafluoroethylene powders, for instance PTFE Ceridust 9205F from Clariant, with a mean size of 8 microns,
  silicone resin powders, for instance the silicone resin Tospearl 145A from GE Silicone, with a mean size of 4.5 microns,
  hollow hemispherical silicone particles, for instance NLK 500, NLK 506 and NLK 510 from Takemoto Oil and Fat,
  acrylic copolymer powders, especially of polymethyl (meth)acrylate, for instance the PMMA particles Jurymer MBI from Nihon Junyoki, with a mean size of 8 microns, the hollow PMMA spheres sold under the name Covabead LH 85 by the company Wackher, and the vinylidene chloride/acrylonitrile/methylene methacrylate expanded microspheres sold under the name Expancel;
  wax powders, for instance the paraffin wax particles MicroEase 114S from MicroPowders, with a mean size of 7 microns,
  polyethylene powders, especially comprising at least one ethylene/acrylic acid copolymer, and in particular consisting of ethylene/acrylic acid copolymers, for instance the Flobeads EA 209 particles from Sumitomo (with a mean size of 10 microns),
  crosslinked elastomeric organopolysiloxane powders coated with silicone resin, especially with silsesquioxane resin, as described, for example, in patent U.S. Pat. No. 5,538,793. Such elastomeric powders are sold under the names KSP-100, KSP-101, KSP-102, KSP-103, KSP-104 and KSP-105 by the company Shin-Etsu,
  polyamide (Nylon®) powders, for instance Nylon 12 particles of the Orgasol type from Atofina, with a mean size of 10 microns,
  powders of polymethyl methacrylate (PMMA) type,
  talc,
  silica/TiO$_2$ or silica/zinc oxide composites,
  styrene/acrylic copolymer powders,
  and mixtures thereof.

Among clays, mention may be made of clays of the smectite family, such as laponite, of the kaolinite family, such as kaolinite, dickite or nacrite, optionally modified clays of the halloysite, dombassite, antigorite, benthierine or pyrophyllite family, montmorillonites, beidellite, vermiculites, talc, stevensite, hectorites, saponites, chlorites, sepiolite and illite.

Clays are products that are already well known per se, which are described, for example, in the publication Minèralogie des argiles [Mineralogy of Clays], S. Caillère, S. Hénin, M. Rautureau, 2nd Edition 1982, Masson, the teaching of which is included herein by way of reference.

Natural clay is a sedimentary rock in large part composed of specific minerals, silicates, generally, of aluminium. Kaolin is thus a natural clay.

The clays may also be synthetic. Thus, Sumecton® mentioned below is a synthetic saponite.

Clays can also be chemically modified by various compounds, such as acrylic acids, polysaccharides (for example carboxymethylcellulose) or organic cations.

Use is preferably made, in the context of the present invention, of clays which are cosmetically compatible with and acceptable to the hair, the skin and/or the scalp.

According to a particularly preferred embodiment of the present invention, the clay used is chosen from kaolinite, montmorillonites, saponites, laponites, hectorites, and illites. Use will more particularly be made of mixtures of clays, and natural clays.

Natural clays that may be mentioned include green clays, in particular rich in illite; clays rich in montmorillonite, known under the name of fuller's earth, or such as bentonites, or also white clays rich in kaolinite. Bentonites that may be mentioned in particular include those sold under the names Bentone 38 VCG, Bentone Gel CAO V, Bentone 27 V and Bentone Gel MIO V by the company Elementis.

As a montmorillonite-rich clay suitable for use in the invention, mention may be made of the hydrated aluminium silicate sold under the name Gel White H® by the company Rockwood.

Mention may be made, as saponite, which belongs to the family of the montmorillonites, of synthetic saponite, in particular that sold by Kunimine under the Sumecton® name.

As regards the silica derivative, silica derivatives not present in the form of a colloidal particle dispersion are preferred in the context of the present invention. In other words, the silica derivatives that may be present in the compositions of the invention are in the form of a dispersion of particles whose numerical mean diameter is greater than or equal to 1 μm.

According to a particular embodiment of the invention, the silicon oxide derivatives whose surface has been chemically modified so as to replace at least some of the silicon atoms with aluminium atoms, forming at least a monomolecular layer of aluminium, are excluded from the definition of the silica derivatives of the invention.

Silica derivatives that may particularly be mentioned include silica powders, for instance the porous silica microspheres sold under the name Silica Beads SB-700 sold by the company Miyoshi, the products Sunsphere® H51, Sunsphere® H33 and Sunsphere® H53 sold by the company Asahi Glass; the polydimethylsiloxane-coated amorphous silica microspheres sold under the name SA Sunsphere® H-33 and SA Sunsphere® H-53 sold by the company Asahi Glass; silica microbeads such as those sold under the name SB150 by the company Miyoshi.

Among the silicate derivatives, mention may be made especially of concave particles based on silicate/silicone copolymers.

In the rest of the description, these particles are referred to as "concave silicone particles".

The concave silicone particles present in the composition according to the invention are in particular particles of hollow sphere portions constituted by a silicone material and more specifically by a silicate/silicone copolymer. The said particles have a mean diameter of less than or equal to 10 μm, especially ranging from 0.1 μm to 8 μm, preferentially from 0.2 to 7 μm, more preferentially ranging from 0.5 to 6 μm and even more preferably ranging from 0.5 to 4 μm.

The term "mean diameter" means the largest dimension of the particle.

The hollow sphere portions used in the composition according to the invention may have the form of truncated hollow spheres, having only one orifice communicating with their central cavity, and having a horseshoe-shaped or bow-shaped cross section.

The organosilicone material is a crosslinked polysiloxane of three-dimensional structure; it preferably comprises, or even is constituted of, units of formula (I): $SiO_2$, and of formula (II): $R_1SiO_{1.5}$
in which $R_1$ denotes an organic group containing a carbon atom directly bonded to the silicon atom. The organic group may be a reactive organic group or an unreactive organic group, and preferably an unreactive organic group.

The unreactive organic group may be a $C_1$-$C_4$ alkyl group, especially a methyl, ethyl, propyl or butyl group, or a phenyl group, and preferably a methyl group.

The reactive organic group may be an epoxy group, a (meth)acryloxy group, an alkenyl group, a mercaptoalkyl, aminoalkyl or haloalkyl group, a glyceroxy group, a ureido group or a cyano group. Preferably, the reactive organic group may be an epoxy group, a (meth)acryloxy group, an alkenyl group or a mercaptoalkyl or aminoalkyl group. The reactive organic group generally comprises from 2 to 6 carbon atoms and especially from 2 to 4 carbon atoms.

According to one preferred embodiment of the invention, bowl-shaped hollow sphere portions are used. These may be obtained as described in patent application JP-2003 128 788.

Horseshoe-shaped hollow sphere portions are also described in patent application JP-A-2000-191 789.

As concave particles of sphere portions that may be used according to the invention, mention may be made of:

bowl-shaped particles consisting of the crosslinked organosilicone TAK-110 (methylsilanol/silicate crosslinked polymer) from the company Takemoto Oil & Fat, of width 2.5 μm, height 1.2 μm and thickness 150 nm (particles sold under the name NLK® 506 by the company Takemoto Oil & Fat);

bowl-shaped particles consisting of the crosslinked organosilicone TAK-110 (methylsilanol/silicate crosslinked polymer) from the company Takemoto Oil & Fat, of width 0.8 μm, height 0.4 μm and thickness 130 nm (particles sold under the name NLK® 515 by the company Takemoto Oil & Fat);

bowl-shaped particles consisting of the crosslinked organosilicone TAK-110 (methylsilanol/silicate crosslinked polymer) from the company Takemoto Oil & Fat, of width 7 μm, height 3.5 μm and thickness 200 nm (particles sold under the name NLK® 510 by the company Takemoto Oil & Fat).

These particles have the CTFA name: methylsilanol/silicate crosspolymer.

Advantageously, the concave silicone particles have a mean diameter of less than or equal to 5 μm, especially ranging from 0.1 μm to 5 μm, preferentially ranging from 0.2 to 5 μm, more preferentially ranging from 0.5 to 4 μm and even more preferably ranging from 0.5 to 3 μm.

These particles with a mean diameter of less than or equal to 5 μm make it possible especially to optimize the glidance, spreading and comfort properties of the composition according to the invention.

Among the silicate derivatives, mention may also be made of annular particles based on silicate/silicone copolymers. In the rest of the description, these particles are referred to as "annular silicone particles".

The annular-shaped silicone particles are preferably chosen from those described and synthesized in patent application US-A-2006/0 089 478. They have a mean outside diameter of from 0.05 to 15 μm and a mean inside diameter of from 0.01 to 10 μm; the difference between the mean outside diameter and the mean inside diameter being from 0.04 to 5 μm.

They have a polysiloxane network comprising siloxane units of formulae (1), (2), (3), (4), (5) and (6):

$$SiO_{4/2} \quad (1)$$

$$Si(OH)_{3/2} \quad (2)$$

$$R_1SiO_{3/2} \quad (3)$$

$$R_2SiO_{3/2} \quad (4)$$

$$R_3Si(OH)O_{2/2} \quad (5)$$

$$R_4Si(OH)O_{2/2} \quad (6)$$

in which:
R1 and R3 denote unreactive hydrocarbon-based groups, and especially R1 and R3 denote alkyl, cycloalkyl, aryl, alkylaryl or aralkyl groups, preferably C1-C3 alkyl groups, especially methyl, ethyl or propyl, and preferentially a methyl group;
and R2 and R4 each denote a hydrocarbon-based group chosen from acryloxy, methacryloxy, vinyl and mercapto groups;
the mole ratio of siloxane units of formula (1)/siloxane units of formulae (2), (3), (4), (5) and (6) being from 20/80 to 50/50; the mole ratio of siloxane units of formulae (2), (3) and (4)/siloxane units of formulae (5) and (6) being from 50/50 to 75/25; and
the mole ratio of siloxane units of formulae (3) and (5)/siloxane units of formulae (4) and (6) being from 20/80 to 60/40.

Acryloxy groups that may be mentioned include a 2-acryloxyethyl group and a 3-acryloxypropyl group.

(Meth)acryloxy groups that may be mentioned include a 2-methacryloxypropyl group and a 3-methacryloxypropyl group.

Vinyl groups that may be mentioned include vinyl, allyl, isopropenyl and 2-methylallyl groups.

Mercapto-bearing groups that may be mentioned include mercaptopropyl and mercaptoethyl groups.

Vinyl groups that may be mentioned include vinyl, allyl, isopropenyl and 2-methylallyl groups.

Hydrophobic silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science, New York, Academic Press, 1990.

The hydrophobic silica aerogel particles used in the present invention have a specific surface area per unit of mass ($S_m$) ranging from 200 to 1500 $m^2/g$, from 500 to 1500 $m^2/g$, preferably from 600 to 1200 $m^2/g$ and better still from 600 to 800 $m^2/g$, and a size expressed as the volume mean diameter (D[0.5]) ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the hydrophobic silica aerogel particles used in the present invention have a size, expressed as volume-mean diameter (D[0.5]), ranging from 1 to 30 μm, preferably from 5 to 25 μm, better still from 5 to 20 μm and even better still from 5 to 15 μm.

The specific surface area per unit of mass can be determined by the nitrogen absorption method, known as the BET (Brunauer-Emmett-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

The sizes of the silica aerogel particles can be measured by static light scattering using a commercial particle size analyser of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, N.C., "Light Scattering by Small Particles", Chapters 9 and 10, Wiley, N.Y., 1957.

According to an advantageous embodiment, the hydrophobic silica aerogel particles used in the present invention have a specific surface area per unit of mass ($S_m$) ranging from 600 to 800 $m^2/g$ and a size, expressed as the volume-mean diameter (D[0.5]), ranging from 5 to 20 μm and even better still from 5 to 15 μm.

The silica aerogel particles used in the present invention may advantageously have a tapped density (p) ranging from 0.04 $g/cm^3$ to 0.10 $g/cm^3$ and preferably from 0.05 $g/cm^3$ to 0.08 $g/cm^3$.

In the context of the present invention, this density may be assessed according to the following protocol, known as the tapped density protocol:

40 g of powder are poured into a measuring cylinder; the measuring cylinder is then placed on the Stay 2003 machine from Stampf Volumeter; the measuring cylinder is subsequently subjected to a series of 2500 tapping actions (this operation is repeated until the difference in volume between 2 consecutive tests is less than 2%); and then the final volume Vf of tapped powder is measured directly on the measuring cylinder. The tapped density is determined by the ratio m/Vf, in this instance 40/Vf (Vf being expressed in $cm^3$ and m in g).

According to one embodiment, the hydrophobic silica aerogel particles used in the present invention have a specific surface area per unit of volume $S_v$ ranging from 5 to 60 $m^2/cm^3$, preferably from 10 to 50 $m^2/cm^3$ and better still from 15 to 40 $m^2/cm^3$.

The specific surface per unit of volume is given by the relationship: SV=SM*p, where p is the tapped density, expressed in $g/cm^3$, and $S_M$ is the specific surface area per unit of mass, expressed in $m^2/g$, as defined above.

Preferably, the hydrophobic silica aerogel particles according to the invention have an oil-absorbing capacity measured at the Wet Point ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method of determination of oil uptake of a powder described in the standard NF T 30-022. It corresponds to the amount of oil adsorbed onto the available surface of the powder and/or absorbed by the powder by measurement of the wet point, described below:

An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added at the rate of one drop at a time and the mixture is subsequently triturated with the spatula.

The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/m.

The aerogels used according to the present invention are hydrophobic silica aerogels, preferably of silylated silica (INCI name: silica silylate).

The term "hydrophobic silica" is understood to mean any silica whose surface is treated with silylating agents, for example with halogenated silanes, such as alkylchlorosilanes, siloxanes, in particular dimethylsiloxanes, such as hexamethyldisiloxane, or silazanes, so as to functionalize the OH groups with silyl groups Si—Rn, for example trimethylsilyl groups.

As regards the preparation of hydrophobic silica aerogel particles modified at the surface by silylation, reference may be made to the document U.S. Pat. No. 7,470,725.

Use will in particular be made of hydrophobic silica aerogel particles surface-modified with trimethylsilyl groups (trimethylsilyl silica).

Mention may be made, as hydrophobic silica aerogels which can be used in the invention, for example, of the aerogel sold under the name VM-2260 (INCI name: Silica silylate) by Dow Corning, the particles of which have a mean size of approximately 1000 microns and a specific surface per unit of mass ranging from 600 to 800 m$^2$/g.

Mention may also be made of the aerogels sold by the company Cabot under the references Aerogel TLD 201, Aerogel OGD 201 and Aerogel TLD 203.

Use will more particularly be made of the aerogel sold under the name VM-2270 (INCI name: Silica silylate) by the company Dow Corning, the particles of which have a mean size ranging from 5 to 15 microns and a specific surface area per unit of mass ranging from 600 to 800 m$^2$/g.

Use will also be made of the aerogel sold under the name Enova® Aerogel MT 1100 (INCI name: Silica silylate) by the company Cabot, the particles of which have a mean size ranging from 2 to 25 microns and a specific surface area per unit of mass ranging from 600 to 800 m$^2$/g.

The mattifying fillers represent from 0.05% to 30% by weight, from 0.1% to 30% by weight, preferably from 0.1% to 20% by weight, better still from 0.2% to 10% by weight, more preferably from 0.5% to 5% by weight or from 1.5% to 5% by weight relative to the total weight of the composition.

Silanes:

The silane(s) that may be used in the composition according to the invention are those corresponding to formula (I) below and/or oligomers thereof:

$$R_1Si(OR_2)_z(R_3)_x(OH)_y \quad (I)$$

in which:
R$_1$ is a linear or branched, saturated or unsaturated C1-C22 hydrocarbon-based chain, which may be substituted with an amine group NH$_2$ or NHR (R=C1-C20 and especially C1-C6 alkyl, C3-C40 cycloalkyl or C6-C30 aromatic); or with a hydroxyl group, a thiol group, an aryl group (more particularly benzyl), which is substituted or unsubstituted; R$_1$ possibly being interrupted with a heteroatom (O, S or NH) or a carbonyl group (CO),
R$_2$ and R$_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2,
with z+x+y=3, The term "oligomer" means the polymerization products of the compounds of formula (I) comprising from 2 to 10 silicon atoms.

Preferably, R$_3$ represents an alkyl group comprising from 1 to 4 carbon atoms, better still a linear alkyl group comprising from 1 to 4 carbon atoms, and preferably methyl or ethyl groups.

Preferably, R$_2$ represents an alkyl group comprising from 1 to 4 carbon atoms, better still a linear alkyl group comprising from 1 to 4 carbon atoms, and preferably the ethyl group.

Preferably, R$_1$ represents an alkyl group, and even more preferentially a linear alkyl group, comprising from 7 to 18 carbon atoms and more particularly from 7 to 12 carbon atoms or a C1-06 and preferably C2-C4 aminoalkyl group.

Preferably, R$_1$ represents an octyl group.

Preferably, z ranges from 1 to 3. Even more preferentially, z is equal to 3.

Preferably, the composition comprises at least one silane chosen from octyltriethoxysilane, dodecyltriethoxysilane, octadecyltriethoxysilane, hexadecyltriethoxysilane and γ-aminopropyltriethoxysilane, preferably chosen from octyltriethoxysilane, dodecyltriethoxysilane, octadecyltriethoxysilane and hexadecyltriethoxysilane.

More particularly, the composition comprises at least octyltriethoxysilane (OTES).

The silane(s) of formula (I) and/or oligomers thereof may be present in the composition of the invention in an active material content ranging from 2% to 20% by weight and preferentially ranging from 5% to 15% by weight relative to the total weight of the composition.

The composition according to the invention comprises an aqueous phase.

The composition according to the invention may be in any galenical form conventionally used for a topical application and especially in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. It may also be in the form of hot-cast sticks or loose or compacted powders.

These compositions are prepared according to the usual methods.

According to one embodiment of the invention, the composition is in the form of an O/W emulsion or an aqueous gel.

The compositions of the invention may be used in any cosmetic or dermatological application, for example in cosmetics for caring for the skin, the hair, the scalp, the eyelashes, the eyebrows, the nails or mucous membranes (the lips), for example as protecting, treating or care products for the face, the hands or the body, as skin-cleansing products (for the face or the body), as makeup products (for example foundations) or as haircare products.

The composition may comprise a fatty phase. When it is present, the proportion of the fatty phase of the emulsion may for example range from 1% to 80% by weight, preferably from 2% to 50% by weight and better still from 5% to 30% by weight relative to the total weight of the composition.

This indicated amount does not comprise the content of lipophilic surfactants.

The nature of the fatty phase (or oily phase) of the emulsion is not critical. The fatty phase may thus consist of any fatty substance conventionally used in cosmetics or dermatology; it especially comprises at least one oil (fatty substance that is liquid at 25° C.).

As oils that may be used in the composition of the invention, examples that may be mentioned include:

- hydrocarbon-based oils of animal origin, such as perhydrosqualene (or squalane);
- hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and the liquid fractions of shea butter;
- synthetic esters and ethers, especially of fatty acids or of fatty alcohols, for instance the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, for instance purcellin oil, isononyl isononanoate, isopropyl myristate, 2-ethylhexyl palmitate (or octyl palmitate), 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; pentaerythritol esters, for instance pentaerythrityl tetraisostearate; and lipophilic amino acid derivatives, such as isopropyl lauroyl sarcosinate (INCI name: Isopropyl Lauroyl Sarcosinate) sold under the name Eldew SL 205 by the company Ajinomoto;
- linear or branched hydrocarbons, of mineral or synthetic origin, such as mineral oils (mixture of hydrocarbon-based oils derived from petroleum; INCI name: Mineral oil), volatile or non-volatile liquid paraffins, and derivatives thereof, petroleum jelly, polydecenes, isohexadecane, isododecane, hydrogenated isoparaffin for instance hydrogenated polyisobutene such as Parleam® oil sold by the company NOF Corporation (INCI name: Hydrogenated Polyisobutene);
- fatty alcohols containing from 8 to 26 carbon atoms, for instance cetyl alcohol, stearyl alcohol and mixtures thereof (cetylstearyl alcohol), octyldodecanol, 2-butyloctanol, 2-hexyldecanol, 2-undecylpentadecanol or oleyl alcohol;
- partially hydrocarbon-based and/or silicone-based fluoro oils, for instance those described in document JP-A-2-295 912;
- cyclic volatile silicone oils, for instance cyclopolydimethylsiloxanes (cyclomethicones) such as cyclopentasiloxane and cyclohexadimethylsiloxane; polydimethylsiloxanes comprising phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyltrimethyl siloxysilicates, and polymethylphenylsiloxanes;
- mixtures thereof.

The other fatty substances that may be present in the oily phase are, for example, fatty acids comprising from 8 to 30 carbon atoms, for instance stearic acid, lauric acid or palmitic acid; gums such as silicone gums (dimethiconol); silicone resins such as trifluoromethyl($C_{1-4}$)alkyl dimethicone and trifluoropropyl dimethicone; pastes such as petrolatum; waxes such as microcrystalline waxes, paraffin waxes, lignite waxes, ceresin, ozokerite, montan wax, beeswax, lanolin and derivatives thereof, candelilla wax, ouricurry wax, carnauba wax, Japan wax, cocoa butter, palm oil in paste form at 20° C., cork fibre wax, sugar cane wax, hydrogenated oils that are solid at 25° C., fatty esters and glycerides that are solid at 25° C., polyethylene waxes, the waxes obtained by Fischer-Tropsch synthesis, and silicone waxes; and mixtures of these fatty substances.

The composition may also optionally comprise a silicone elastomer (silicone elastomers or elastomeric organopolysiloxane). The term "elastomer" is understood to mean a deformable, flexible solid material having viscoelastic properties and in particular the consistency of a sponge or of a flexible sphere. Its modulus of elasticity is such that this material withstands deformation and has a limited ability to extend and to contract. This material is capable of regaining its original shape after stretching. This elastomer is formed from polymer chains of high molecular weight, the mobility of which is limited by a uniform network of crosslinking points.

Elastomeric organopolysiloxanes are generally partially or completely crosslinked and may be in the form of particles.

Such elastomers are, for example, the products sold under the name KSG by the company Shin-Etsu, under the name Trefil by the company Dow Corning or under the name Gransil by the company Grant Industries.

The composition according to the invention comprises an aqueous phase, the amount of which may range, for example, from 30% to 98% by weight, preferably from 40% to 98% by weight, better still from 50% to 98% by weight and even better still from 55% to 98% by weight relative to the total weight of the composition.

Conventionally, the aqueous phase may contain, besides water, one or more water-soluble solvents chosen from polyols (or polyhydric alcohols) and water-soluble lower alcohols, and mixtures thereof. The term "lower alcohol" means an alcohol comprising from 1 to 8 and preferably from 1 to 6 carbon atoms. Examples of lower alcohols that may be mentioned include ethanol, isopropanol and butanol, and mixtures thereof.

Examples of polyols that may be mentioned include glycerol; glycols such as propylene glycol or butylene glycol; sorbitol; sugars such as glucose, fructose, maltose, lactose and sucrose; and mixtures thereof.

The amount of water-soluble solvents (polyols and lower alcohols) may range, for example, from 0.5% to 30% by weight, preferably from 0.5% to 20% by weight and better still from 1% to 15% by weight relative to the total weight of the composition.

Adjuvants

In a known manner, the composition of the invention may also contain adjuvants that are common in cosmetics and/or dermatology, such as active agents, preserving agents, antioxidants, complexing agents, pH modifiers (acidic or basic), fragrances, fillers, bactericides, odour absorbers, colorants (pigments and dyes), film-forming polymers, emulsifiers such as fatty acid esters of polyethylene glycol, fatty acid esters of glycerol and fatty acid esters of sorbitan, which are optionally polyoxyethylenated, polyoxyethylenated fatty alcohols and fatty acid esters or ethers of sugars such as sucrose or glucose; thickeners and/or gelling agents, in particular polyacrylamides, acrylic homopolymers and copolymers, and acrylamidomethylpropanesulfonic acid homopolymers and copolymers, and also lipid vesicles. The amounts of these various adjuvants are those conventionally used in the field under consideration, for example from 0.01% to 20% of the total weight of the composition. Depending on their nature, these adjuvants may be introduced into the fatty phase, into the aqueous phase and/or into the lipid vesicles.

Needless to say, a person skilled in the art will take care to select this or these optional additional compounds, and/or the amount thereof, such that the mattifying/soft focus properties of the composition according to the invention are not, or are not substantially, adversely affected by the envisaged addition.

In the patent application, unless specifically mentioned otherwise, the contents are expressed on a weight basis relative to the total weight of the composition.

The examples that follow are aimed at illustrating the compositions and processes according to this invention, but are not in any way a limitation of the scope of the invention. All the parts and percentages in the examples are given on a weight basis and all the measurements were obtained at about 25° C., unless otherwise mentioned.

EXAMPLE 1

The following compositions were prepared:

|  | A | B* |
|---|---|---|
| PHASE A | | |
| Water | qs 100 | qs 100 |
| Preserving agents | qs | qs |
| PHASE B | | |
| Glycerol | 10 | 10 |
| Sodium polyacrylate (Cosmedia SP from Rhodia) | 0.5 | 0.5 |
| PHASE C | | |
| Octyltriethoxysilane | | 10 |
| Polydimethylsiloxane 5 cSt | 10 | |
| Glyceryl stearate (and) PEG-100 stearate (Arlacel 165-FL from Uniqema) | 2 | 2 |
| PHASE D | | |
| Perlite | 1 | 1 |
| PHASE E | | |
| Denatured ethanol | 7 | 7 |

*Composition according to the invention

Procedure:

Once the preserving system has been dissolved in water (at the necessary temperature), add phase B to phase A with stirring using a Rayneri blender. Homogenize phase C (at the temperature necessary to have a homogeneous liquid phase). When the mixtures (A+B) and C are homogeneous, form the emulsion in a conventional manner by adding C to (A+B) with stirring using a Rayneri blender. Homogenize until a smooth gel is obtained. Add D and homogenize for 5 minutes at 1000 rpm and then introduce E.

For each of the compositions, the cosmetic properties were evaluated according to the following protocol.

The cosmetic properties on application are evaluated, monadically, by a panel of experts trained in the description of care products. The sensory evaluation of the care products by this panel is performed as follows: the products are conditioned in opaque jars or pump-dispenser bottles depending on the viscosity of the products.

Within the same session, the samples are presented in random order to each panellist. Fifteen experts evaluated the glidance in the following manner: on a hand precleaned with water and liquid soap and wiped dry with a tissue, 0.05 ml of product is applied to the top half of the hand (five cycles with the index and middle fingers). The product is evaluated during the five passes, and 2 minutes after application.

The experts evaluated the following parameters:
Glidance on application
The final softness and comfort of the skin, after penetration The descriptors were evaluated on a scale at five levels: None, Sparingly, Moderately, Quite, Very.

The descriptor "glidance" is defined as being the ease of application of the product, its ability to cover a defined area and the capacity of the product not to drag on the skin during application.

Results obtained on a panel of 15 experts:

| Formulation | A | B* |
|---|---|---|
| Glidance on application | 3/15: none<br>12/15: sparingly | 2/15: quite<br>13/15: very |
| Softness of the application skin | Sparingly (10/15)<br>None (5/15) | Very (14/15)<br>Quite (1/15) |

The comparative evaluation of these two formulations shows that the formulation according to the invention (formulation B*) spreads more easily and makes the skin softer at the end when compared with the silane-free formulation.

EXAMPLE 2

An emulsion containing a clay was prepared.

|  | A | B* |
|---|---|---|
| PHASE A | | |
| Water | qs 100 | qs 100 |
| Preserving agents | qs | qs |
| PHASE B | | |
| Glycerol | 10 | 10 |
| Montmorillonite (Kunipia G4 from Kunimine) | 5 | 5 |
| PHASE C | | |
| Octyltriethoxysilane | | 5 |
| Hydrogenated polyisobutene | 5 | 5 |
| Glyceryl stearate (and) PEG-100 stearate (Arlacel 165 from Croda) | 3 | 3 |

*Composition according to the invention

Procedure:

Using a Rayneri blender, delaminate the montmorillonite for one hour in a sufficient amount of water, while keeping it hot (phase B). As regards phase A, once the preserving system has been dissolved in water (at the necessary temperature), add phase A to phase B with stirring using a Rayneri blender. Homogenize phase C (at the temperature necessary—water bath—to have a homogeneous liquid phase). Emulsify: phase (A+B) in phase C with a mixer. Cool in a bath of ice+water with Rayneri blending.

Results obtained on a panel of 15 experts:

| Formulation | A | B* |
|---|---|---|
| Glidance on application | 3/15: none<br>12/15: sparingly | 2/15: quite<br>13/15: very |
| Skin softness after penetration | Sparingly (9/15)<br>None (6/15) | Very (14/15)<br>Quite (1/15) |

The comparative evaluation of these two formulations shows that the formulation according to the invention (formulation B*) spreads more easily and makes the skin softer at the end when compared with the silane-free formulation.

EXAMPLE 3

A moisturizing gel for greasy skin was prepared.

| PHASE A | |
|---|---|
| Water | qs 100 |
| Preserving agents | qs |
| Glycerol | 10 |
| Moisturizing active agents | 5 |
| Ammonium polyacryloyldimethyl taurate (Hostacerin AMPS ® from Clariant) | 2 |
| PHASE B | |
| Octyltriethoxysilane | 8 |
| DICAPRYLYL CARBONATE | 5 |
| Glyceryl stearate (and) PEG-100 stearate (Arlacel 165 from Croda) | 1 |
| PHASE C | |
| Methylsilanol/silicate crosspolymer (NLK 506 from Takemoto) | 3 |
| Silica microspheres (Silica Beads SB700 from Miyoshi Kasei) | 1.5 |

Procedure:

Homogenize phases A and B at 70° C. Emulsify by pouring the fatty phase B into the aqueous phase. Cool to room temperature and disperse the fillers with stirring of Rayneri turbomixer type.

A cream gel that is pleasant to apply is obtained, which leaves the skin soft, matt and moisturized.

EXAMPLE 4

The following composition was prepared:

| | A | B (invention) |
|---|---|---|
| PHASE A | | |
| Water | qs 100 | qs 100 |
| Preserving agents | qs | qs |
| PHASE B | | |
| Glycerol | 10 | 10 |
| Sodium polyacrylate (Cosmedia SP from Rhodia) | 0.5 | 0.5 |
| PHASE C | | |
| Octyltriethoxysilane | — | 10 |
| Polydimethylsiloxane 5 cSt | 10 | — |
| Glyceryl stearate (and) PEG-100 stearate (Arlacel 165 from Croda) | 2 | 2 |

| | A | B (invention) |
|---|---|---|
| PHASE D | | |
| Hydrophobic silica aerogel (VM-2270 from Dow Corning) | 1 | 1 |
| PHASE E | | |
| Denatured ethanol | 7 | 7 |

Procedure:

Once the preserving system has been dissolved in water (at the necessary temperature), add phase B to phase A with stirring using a Rayneri blender. Homogenize phase C (at the temperature necessary to have a homogeneous liquid phase). When the mixtures (A+B) and C are homogeneous, form the emulsion in a conventional manner by adding C to (A+B) with stirring using a Rayneri blender. Homogenize until a smooth gel is obtained. Add D and homogenize for 5 minutes at 1000 rpm and then introduce E.

For each of the compositions, the cosmetic properties were evaluated according to the following protocol.

The cosmetic properties on application are evaluated, monadically, by a panel of experts trained in the description of care products. The sensory evaluation of the care products by this panel is performed as follows: the products are conditioned in opaque jars or pump-dispenser bottles depending on the viscosity of the products.

Within the same session, the samples are presented in random order to each panellist. Fifteen experts evaluated the glidance in the following manner: on a hand precleaned with water and liquid soap and wiped dry with a tissue, 0.05 ml of product is applied to the top half of the hand (five cycles with the index and middle fingers). The product is evaluated during the five passes, and 2 minutes after application. The experts evaluated the following parameters:

Glidance on application the coarse effect on application (which induces difficulty in application)

The final softness and comfort of the skin, after penetration

The descriptors are evaluated on a scale at five levels: None, Sparingly, Moderately, Quite, Very.

The descriptor "glidance" is defined as being the ease of application of the product, its ability to cover a defined area and the capacity of the product not to drag on the skin during application.

Results obtained on a panel of 15 experts:

| Formulation | A | B* |
|---|---|---|
| Glidance on application | 2/15: none<br>13/15: sparingly | 3/15: quite<br>12/15: very |
| Rasping/coarse effect on application | Very (12/15)<br>Quite (3/12) | None (13/15)<br>Sparingly (2/15) |
| Comfort/softness after penetration | Sparingly (8/15)<br>None (7/15) | Very (14/15)<br>Quite (1/15) |

The comparative evaluation of these two formulations indicates that the formulation according to the invention (formulation B*) spreads very easily on application when compared with the formulation containing a volatile silicone in place of the silane. There is no rasping effect and the skin is very soft after application and drying of the composition according to the invention.

The invention claimed is:

1. A cosmetic process for treating skin, wherein scalp is excluded from the skin to be treated which comprises applying to the skin a cosmetic composition comprising:
   an aqueous phase,
   at least one mattifying filler, which are chosen from hydrophobic silica aerogel particles, and
   at least one silane corresponding to formula (I) below and/or oligomer thereof:

$$R_1Si(OR_2)_z(R_3)_x(OH)_y \quad (I)$$

in which:
   $R_1$ represents an alkyl group comprising from 7 to 18 carbon atoms,
   $R_2$ represents lower alkyl group comprising from 1 to 4 carbon atoms
   $R_3$ represents lower alkyl group comprising from 1 to 4 carbon atoms
   z is equal to 3
   y and x are equal to 0
   the at least one silane of formula (I) and/or oligomer thereof is present from 2% to 20% by weight relative to the total weight of the composition.

2. The cosmetic process according to claim 1, wherein the cosmetic composition comprises at least octyltriethoxysilane.

3. The cosmetic process according to claim 1, wherein the silane(s) of formula (I) and/or oligomers thereof are present in a content ranging from 5% to 15% by weight relative to the total weight of the composition.

4. The cosmetic process according to claim 1, wherein the at least one mattifying filler are chosen from hydrophobic aerogel particles with a specific surface area per unit of mass (SM) ranging from 200 to 1500 m²/g, and a size expressed as the volume mean diameter (D[0.5]) ranging from 1 to 30 μm and/or an oil-absorbing capacity measured at the Wet Point ranging from 5 to 18 ml/g of particles.

5. The cosmetic process according claim 1, wherein the at least one mattifying filler represent from 0.05% to 30% by weight relative to the total weight of the composition.

6. The cosmetic process according to claim 1, wherein $R_2$ represents an ethyl group, and $R_3$ represents methyl or ethyl groups.

7. The cosmetic process according to claim 1, wherein $R_1$ represents an octyl group.

8. The cosmetic process according to claim 1, wherein the cosmetic composition comprises at least one silane selected from the group consisting of octyltriethoxysilane, dodecyltriethoxysilane, octadecyltriethoxysilane and hexadecyltriethoxysilane.

* * * * *